United States Patent [19]

von Plessen et al.

[11] Patent Number: 4,925,959
[45] Date of Patent: May 15, 1990

[54] DIOXANE ADDUCT OF 2-HYDROXYNAPHTHALENE-6-CARBOXYLIC ACID AND PROCESS FOR THE PREPARATION THEREOF

[75] Inventors: Helmold von Plessen, Königstein/Taunus; Siegbert Rittner, Mörfelden-Walldorf, both of Fed. Rep. of Germany

[73] Assignee: Hoechst Aktiengesellschaft, Frankfurt am Main, Fed. Rep. of Germany

[21] Appl. No.: 349,579

[22] Filed: May 9, 1989

[30] Foreign Application Priority Data

May 10, 1988 [DE] Fed. Rep. of Germany ....... 3815929

[51] Int. Cl.$^5$ ............................................ C07D 319/12
[52] U.S. Cl. ...................................... 549/377; 562/467
[58] Field of Search ......................... 549/377; 562/467

[56] References Cited

U.S. PATENT DOCUMENTS

| | | | |
|---|---|---|---|
| 4,329,494 | 5/1982 | Montgomery | 562/425 |
| 4,393,191 | 7/1983 | East | 528/207 |
| 4,618,701 | 10/1986 | Neeb et al. | 562/467 |

OTHER PUBLICATIONS

Tanonaka et al., C.A., 106—120361x (1987).

*Primary Examiner*—Nicky Chan

[57] ABSTRACT

The invention relates to the dioxane adduct of 2-hydroxynaphthalene-6-carboxylic acid which adduct comprises 1 mol of 1,4-dioxane and about 2 mol of 2-hydroxynaphthalene-6-carboxylic acid per mol. The invention further relates to a process for the preparation of this adduct, wherein the 2-hydroxynaphthalene-6-carboxylic acid is dissolved in dioxane or a mixture thereof with water or with an organic solvent and then allowed to crystallize.

1 Claim, No Drawings

DIOXANE ADDUCT OF 2-HYDROXYNAPHTHALENE-6-CARBOXYLIC ACID AND PROCESS FOR THE PREPARATION THEREOF

DESCRIPTION

2-Hydroxynaphthalene-6-carboxylic acid is produced industrially by a modified Kolbe-Schmitt reaction. In this process the potassium salt of 2-naphthol is reacted under pressure at 200°–300° C. with carbon dioxide (US-PS 4,329,494, EP-PS 53,824, US-PS 1,593,816, US-PS 4,287,357 and EP-PS 81,753). This reaction gives rise to considerable amounts of decomposition products (tars and resins) which are difficult to separate off, as are the byproducts (2-hydroxynaphthalene-3-carboxylic acid and 2-hydroxynaphthalene-3,6-dicarboxylic acid) also formed.

After separation of 2-naphthol, the crude acid has hitherto been worked up in a costly manner, viz. by extraction, adsorption on carbon and precipitation from water.

It has now been found that 2-hydroxynaphthalene-6-carboxylic acid (abbreviated in the following to "2,6-acid") can be reacted with 1,4-dioxane to form an adduct which comprises about 2 mol of 2,6-acid and 1 mol of dioxane per mol. The adduct crystallizes from dioxane-containing solution in the form of well-formed column-like and plate-like crystals which can be separated from the mother liquor by sedimentation, filtration or centrifugation.

One subject of the invention is this adduct itself. A further subject is a process for the preparation of an adduct from 2-hydroxynaphthalene-6-carboxylic acid and 1,4-dioxane, wherein 2-hydroxynaphthalene-6-carboxylic acid is dissolved in 1,4-dioxane or a mixture thereof with water or with an organic solvent and then allowed to crystallize.

Industrial 2,6-acid may be used directly for the preparation of the adduct.

The 2,6-acid is preferably dissolved in a mixture of 1,4-dioxane and water having a 20–90% by weight dioxane content with heating and is subsequently allowed to crystallize out on cooling. The crystalline product is, for example, filtered off and dried at about 50° C. in vacuo in a stream of nitrogen.

Instead of a mixture of dioxane with water, a mixture of dioxane with an organic solvent may also be used. It is even possible to use water and organic solvents miscible with it at the same time as components of the mixture; for example, the dioxane adduct may be allowed to crystallize out from a ternary mixture of dioxane/water/lower alcohols or dioxane/water/polyethylene glycols. The dioxane content of the mixtures with water and/or organic solvents is generally at least 10% by weight, preferably at least 20% by weight, in particular at least 30% by weight.

The adduct may be stored indefinitely at room temperature. If it is desired to recover dioxane-free 2,6-acid therefrom, it is sufficient to heat the adduct to about 100° C. in vacuo. In this way the loosely bound dioxane is virtually completely split off, furnishing pure 2,6-acid as amorphous white powder or finely divided granules. Dioxane-free 2,6-acid may also be recovered by recrystallization of the adduct from another solvent, for example dilute ethanol. Dioxane-free 2,6-acid may furthermore be obtained by dissolving the adduct in sodium hydroxide solution, followed by precipitation with dilute mineral acid.

The special properties of the adduct according to the invention make it a valuable intermediate. Thus, 2-hydroxynaphthalene-6-carboxylic acid which could previously be isolated in pure form from the reaction products of the Kolbe-Schmitt reaction only with difficulty, can be prepared in a high degree of purity via the adduct. The possibility of virtually completely freezing 2,6-acid from impurities such as 2-hydroxynaphthalene-3-carboxylic acid, 2-hydroxynaphthalene-3,6-dicarboxylic acid and 2-naphthol which are formed in the synthesis as byproducts, via the adduct, represents a surprising step forward compared with the conventional troublesome process for purification of carboxylic acids. Thus, for example according to US-PS 2,189,726, carboxylic acids may be purified by multi-stage washing with water and heating or by steam distillation.

The adduct may be employed as coupling component for azo dyes, 1 mol of adduct being reacted with 2 mol of a diazo component. The dioxane set free in the reaction may be used to dilute and homogenize the reaction mixture.

The adduct is of special significance for the production of very pure 2-hydroxynaphthalene-6-carboxylic acid ("fiber grade" quality), required for polyesterification with organic hydroxycarboxylic acids such as p-hydroxybenzoic acid. The pure polyesters obtained in this manner are valuable starting materials for the preparation of plastics or fibers (US-PS 4,393,191).

EXAMPLES 50 parts of crude 2-hydroxynaphthalene-6-carboxylic acid (obtained by the Kolbe-Schmitt method) were dissolved in a mixture of 400 parts of water and 300 parts of 1,4-dioxane with stirring and heating. The mixture was mixed with 5 parts of activated carbon and filtered. The solution was allowed to cool slowly. The separated crystals of the adduct were filtered off and washed with 30% dioxane. It was then recrystallized from a mixture of 360 parts of water and 270 parts of dioxane. The product was dried in vacuo over concentrated sulfuric acid. Melting point (after recrystallization from dilute ethanol): 247°–248° C.

| Analysis (in % by weight): | C | H |
|---|---|---|
| calculated | 67.24% | 5.2% |
| found | 67.15% | 5.2% |

| | | Content of impurities in the starting product and the end product (% by weight) | | | | |
|---|---|---|---|---|---|---|
| | | 2-hydroxy-naphthalene-3,6-dicarboxylic acid | 2-hydroxy naphthalene-3-carboxylic acid | 2-naphthol | 2,2-dihydroxy 1,1'-dinaphthyl | Color value |
| Example | Starting | 0.421 | 0.227 | 0.065 | 0.018 | $21.0 \times 10^{-6}$ |

-continued

| | | Content of impurities in the starting product and the end product (% by weight) | | | | |
|---|---|---|---|---|---|---|
| | | 2-hydroxy-naphthalene-3,6-dicarboxylic acid | 2-hydroxy naphthalene-3-carboxylic acid | 2-naphthol | 2,2-dihydroxy 1,1'-dinaphthyl | Color value |
| 1 | product End product | 0.018 | <0.05 | <0.05 | <0.05 | $1.8 \times 10^{-6}$ |
| Example 2 | Starting product | 1.762 | 0.719 | 0.225 | <0.05 | $60.9 \times 10^{-6}$ |
| | End product | 0.085 | <0.05 | 0.014 | <0.05 | $1.8 \times 10^{-6}$ |

EXAMPLE 3

12.5 parts of crude 2,6-acid were dissolved in a mixture of 42 parts of glacial acetic acid and 41 parts of dioxane with stirring and heating. The mixture was mixed with 1 part of activated carbon, stirred for 2 minutes and then filtered. The crystalline adduct separated from the solution on slow cooling; it was filtered off and washed with 20% by weight of ethanol. Drying in vacuo over concentrated sulfuric acid furnished 11.3 parts of the adduct.

We claim:
1. A dioxane adduct of 2-hydroxynaphthalene-6-carboxylic acid containing about 2 mol of 2-hydroxynaphthalene-6-carboxylic acid per mol of 1,4-dioxane.

* * * * *

UNITED STATES PATENT AND TRADEMARK OFFICE
CERTIFICATE OF CORRECTION

PATENT NO. : 4,925,959

DATED : May 15, 1990

INVENTOR(S) : HELMOLD VON PLESSEN, ET AL.

It is certified that error appears in the above-identified patent and that said Letters Patent is hereby corrected as shown below:

```
Column 2, line 16   "freezing" should read

-- freeing -- .
```

Signed and Sealed this

Fifth Day of January, 1993

Attest:

DOUGLAS B. COMER

*Attesting Officer*          *Acting Commissioner of Patents and Trademarks*